United States Patent [19]

Atsumi et al.

[11] Patent Number: 5,348,577
[45] Date of Patent: * Sep. 20, 1994

[54] ANTIBACTERIAL CALCIUM TERTIARY PHOSPHATE

[75] Inventors: Kiminori Atsumi; Tomoki Saito; Masaaki Komori, all of Tokyo, Japan

[73] Assignee: Kabushiki Kaisha Sangi, Tokyo, Japan

[*] Notice: The portion of the term of this patent subsequent to Sep. 29, 2009 has been disclaimed.

[21] Appl. No.: 967,067

[22] Filed: Oct. 28, 1992

[30] Foreign Application Priority Data

Oct. 31, 1991 [JP] Japan .................. 3-311417

[51] Int. Cl.$^5$ .................. A61K 33/38; A61K 33/30; A61K 33/34
[52] U.S. Cl. .................. 106/18.31; 106/18.36; 106/35; 106/462; 424/602; 424/604; 424/618; 424/641; 501/1; 502/340
[58] Field of Search .............. 501/1; 106/18.31, 18.36, 106/35, 462; 424/602, 604, 618, 641; 502/340

[56] References Cited

U.S. PATENT DOCUMENTS 5,009,898 4/1991 Sakuma et al. .................. 106/35
5,151,122 9/1992 Atsumi et al. .................. 106/35

FOREIGN PATENT DOCUMENTS 4134540 4/1993 Fed. Rep. of Germany .
60-181002 9/1985 Japan .
2-180270 7/1990 Japan .
3200702 9/1991 Japan .
4142340 5/1992 Japan .
2238044 5/1991 United Kingdom .

OTHER PUBLICATIONS 92-213361, Oct. 1990, (Derwent Publications Ltd.).
91-300219, Dec. 1989, (Derwent Publications Ltd.).

Primary Examiner—Mark L. Bell
Assistant Examiner—Deborah Jones
Attorney, Agent, or Firm—Finnegan, Henderson, Farabow, Garret & Dunner

[57] ABSTRACT

A calcium tertiary phosphate is used as a carrier, and the carrier is caused to carry silver and zinc. The result is an antibacterial ceramic exhibiting an ultra high degree of whiteness and suppressed discoloration. This material may be heat fired at a temperature above 960° C. to obtain a further improvement.

4 Claims, No Drawings

ANTIBACTERIAL CALCIUM TERTIARY PHOSPHATE

BACKGROUND OF THE INVENTION

Field of the Invention

This invention relates to an antibacterial calcium tertiary phosphate. More particularly, the invention relates to calcium tertiary phosphate made to carry silver and zinc and/or ions thereof, wherein calcium tertiary phosphate is safe, exhibits a high degree of whiteness and resist discoloration to the maximum extent.

Description of the Prior Art

It is known that metals such as silver and zinc as well as ions and salts of these metals exhibit a strong antibacterial property, and various processes have been proposed for utilizing these. However, when these metals are used as is in mixture with a substrate such as resin, fibers or paint, problems arise involving dispersibility with respect to the substrate, the eluting property of the metal ions, tinting and discoloration. For this reason, use in wide fields of application has not been possible.

Substances in which antibacterial metals, metal salts or metal ions are carried on highly safe ceramics have recently been proposed as substances which utilize the antibacterial property of the abovementioned metals. For example, antibacterial ceramics, in which the antibacterial metal ions are carried on zeolite, is disclosed in Japanese Patent Laid Open Publication Sho 60-181002 and antibacterial ceramics, in which the antibacterial metal ions are carried on hydroxyapatite, is disclosed in Japanese Patent Laid Open Publication Hei 2-180270. Since these substances exhibit reduced elution of the carried antibacterial metal ions into water and have improved dispersibility with respect to the substrate, they can be utilized comparatively safely and in many fields of application. However, depending upon the medium used, even these substances undergo elution of their metal ions into the medium, and therefore they cannot always be used with complete safety in all types of media.

Generally, silver is used as the antibacterial metal, because silver has strong antibacterial property. However, it is known that silver generally is sensitive to light and will break down and change color to gray or black when exposed to light. Accordingly, silver salts undergo discoloration when used as is. Antibacterial agents in which this metal salt is carried on ceramics or the like can lead to problems not only in terms of discoloration but also in terms of safety since the elution of silver from the silver salt and the release of silver salt from the ceramics cannot be reasonably prevented.

Though zeolite made to carry silver by means of ion exchange exhibits less discoloration in comparison to those cases where the silver salt is used as is, discoloration with the passage of time is unavoidable. In comparison with zeolite carrying silver, hydroxyapatite made to carry silver by ion exchange is much improved in terms of discoloration attributable to the silver, but complete suppression of discoloration has still not been realized.

Studies have been conducted with a view to improving upon the foregoing, and processes for carrying zinc along with silver on hydroxyapatite and further heat-firing has been considered. However, in cases where zinc is carried together with silver, the antibacterial hydroxyapatite tends to become light gray in color as the amount of silver carried is increased, and even though the color is close to white, the degree of whiteness is low. In addition, discoloration cannot be completely suppressed over an extended period of time. In cases where heat-firing is carried out, discoloration can be suppressed. Nevertheless, the antibacterial agent itself still becomes light brown in color and the degree of whiteness diminishes as the amount of silver carried increases. These problems arise when silver is used as the antibacterial metal, and though improvements have been made by carrying zinc and silver on hydroxyapatite and heat firing thereof, these still have not been resolved the problem totally.

SUMMARY OF THE INVENTION

Accordingly, an object of the present invention is to provide antibacterial calcium tertiary phosphate, which exhibits a high degree of whiteness, will not undergo discoloration even when stored for very long periods of time, and in which safe calcium tertiary phosphate is used as the carrier.

As mentioned above, an antibacterial agent obtained by having hydroxyapatite carry silver and zinc and/or ions thereof or subsequently being heat-fired is an easy-to-use antibacterial material which also exhibits excellent dispersibility in substrates, discoloration has been seen with the passage of time, and the antibacterial agent becomes light brown in color as a result. As a consequence, problems arise in terms of storage of the antibacterial agent and the color of manufactured articles produced with use of the agent, and therefore the fields of application are limited. Also, when the antibacterial agent, in which silver and zinc are carried on a carrier selected from calcium primary phosphate, calcium secondary phosphate and calcium pyro phosphate, and then heat-fired the problems in terms of discoloration, tinting, using and storing are overcome in comparison to using hydroxyapatite as the carrier.

Accordingly, the inventors have devoted research to silver-containing inorganic antibacterial agents which exhibit an ultra high degree of whiteness and will not undergo discoloration. As a result of this research, the inventors have been able to obtain an antibacterial agent which attains the foregoing objects. Specifically, by using calcium tertiary phosphate as the carrier and causing this carrier to carry silver and zinc, an antibacterial agent exhibiting an ultra high degree of whiteness and substantially suppressed discoloration has been obtained. By heat-firing calcium phosphate, which has been made to carry silver and zinc, at a temperature above 960° C., an antibacterial agent which exhibits a superior degree of whiteness higher than that of the heat-fired antibacterial hydroxyapatite, and which will not undergo discoloration, has been obtained.

More specifically, a prescribed amount of calcium tertiary phosphate is added to an aqueous solution, in which the prescribed amounts of silver and zinc salts are dissolved. The mixture is stirred. After sufficient stirring, precipitates are filtered out and the product is washed thoroughly with distilled water and then dried, whereby there is obtained an antibacterial calcium tertiary phosphate.

The degree of whiteness of the obtained antibacterial calcium tertiary phosphate ceramics naturally is influenced by the amount of silver carried, just as it is influenced by the adsorption retention ratio of the silver and zinc. That is, in order to obtain an antibacterial calcium tertiary phosphate exhibiting a superior high degree of whiteness and no change in color with the passage of time, the amount of silver adsorbed and retained should be no more than 10% by weight, and preferably no more than 5% by weight, with respect to the calcium tertiary phosphate. On the other hand, in consideration of antibacterial capability, the amount of silver retained preferably is no less than 0.0001%. When the amounts of silver carried on hydroxyapatite are over 0.1% in the antibacterial hydroxyapatite, even if zinc coexists, the color becomes bad, and discoloration occurs with the passage of time.

However, when calcium tertiary phosphate is used as the carrier, change in color is less. A change in color with the passage of time can be suppressed even further by heat-firing the product at a temperature above 961° C., which is the melting point of silver. The amount of zinc retained in coexistence with silver is required to be at least 5% by weight with respect to the amount of silver retained. The amount of zinc retained can be selected at will.

DETAILED DESCRIPTION OF THE INVENTION

An example of the present invention will now be described in detail.

EXAMPLE 1

1.0 kg of calcium tertiary phosphate, 0.002 of silver nitrate and 47 g of zinc nitrate were added to 10 l of distilled water and stirred. The product was filtered out, washed throughly with distilled water and dried and a portion of the resulting product was powdered to obtain an antibacterial calcium tertiary phosphate carrying silver, about 0.0001% and zinc, about 1% (1-1). The remainder of this product was heat-fired at 960° C., and powdered to obtain an antibacterial calcium tertiary phosphate carrying silver, about 0.0001% and zinc, about 1% (1-2).

EXAMPLE 2

1.0 kg of calcium tertiary phosphate, 2 g of silver nitrate and 0.24 g of zinc nitrate were added to 10 l of distilled water and stirred. The product was filtered out, washed throughly with distilled water, and dried, and a portion of the resulting product was powdered to obtain an antibacterial calcium tertiary phosphate carrying silver, about 0.1% and zinc, about 0.005% (2-1). The remainder of this product was heat-fired at 1,000° C. and powdered to obtain an antibacterial calcium tertiary phosphate carrying silver, about 0.1% and zinc, about 0.005% (2-2).

EXAMPLE 3

1.0 kg of calcium tertiary phosphate, 34 g of silver nitrate and 93 g of zinc nitrate were added to of distilled water and stirred. The product was filtered out, washed throughly with distilled water, and dried. A portion of the resulting product was powdered and an antibacterial calcium tertiary phosphate carrying silver, about 2% and zinc, about 2% was obtained (3-1). Also the remainder of this product was heat-fired at 1,200° C. and powdered. An antibacterial calcium tertiary phosphate carrying silver, about 2% and zinc, about 2% was obtained (3-2).

EXAMPLE 4

1.0 kg of calcium tertiary phosphate, 82 g of silver nitrate and 140 g of zinc nitrate were added to 10 l of distilled water and stirred. The product was filtered out, washed throughly with distilled water, dried. A portion of the resulting product was powdered and an antibacterial calcium tertiary phosphate carrying silver, about 5% and zinc, about 3% was obtained (4-1). Also the remainder was heat-fired at 1,200° C. and powdered. An antibacterial calcium tertiary phosphate carrying silver, about 5% and zinc, about 3% was obtained (4-2).

EXAMPLE 5

1.0 kg of calcium tertiary phosphate, 165 g of silver nitrate and 233 g of zinc nitrate were added to 10 l of distilled water and stirred. The product was filtered out, washed thoughly with distilled water and dried. A portion of the resulting product was powdered and an antibacterial calcium tertiary phosphate carrying silver, about 10% and zinc, about 5% was obtained (5-1). The remainder of this product was heat fired at 1,200° C. and powdered. An antibacterial calcium tertiary phosphate carrying silver, about 10% and zinc, about 5% was obtained (5-2).

EXAMPLE 6

Antibacterial Test

A solution containing $4.7 \times 10^5$ colon bacilli was added to a phosphate buffer solution, in which 1 weight % of each of the samples obtained in examples 1 to 5 was added, and the antibacterial property against the colon bacilli was measured for each sample. The result of measurement was that absolutely no bacteria was detected in 24 hours.

EXAMPLE 7

Degree of Whiteness Test

A spectrophotometer was used to measure the degree of whiteness degree of the antibacterial calcium tertiary phosphate powders produced in examples 1 to 5. Barium sulfate was used as the standard substance. As the control, hydroxyapatites carrying silver and zinc were prepared by the same way as shown in each example in which hydroxyapatite is used in place of calcium tertiary phosphate. ((Nonheat fired (control 1-1 to control 5-1), heat-fired (control 2-1 to control 2-5)) and the degree of whiteness was measured. Further, the degree of whiteness of these samples was measured after letting them stand in a bright room for 6 months. Similarly, nonheat fired and heat fired calcium tertiary phosphates carrying only silver (Nonheat fired (T1-1 to T5-1) and heat fired (T1-2 to T5-2)) and nonheat fired and heat fired hydroxyapatites carrying only silver (Nonheat fired (H1-1 to H5-1) and heat fired (H1-2 to H5-2)) were prepared, and the degree of whiteness was measured.

The results obtained are shown in Table 1.

The effects for the degree of whiteness and discoloration are clear when calcium tertiary phosphate is used as the carrier.

Comparison Example

Calcium secondary phosphate carrying silver 2%, calcium pyro phosphate carrying silver 2%, the heat fired bodies thereof which were heat fired at 1,200° C., calcium secondary phosphate carrying silver, 2% and zinc, 2%, calcium pyro phosphate carrying silver, 2% and zinc, 2%, and heat fired bodies thereof which were heat-fired at 1,200° C. were prepared and the whiteness degree was measured. The results are shown in Table 2.

TABLE 1

| sample | measured value Degree of whiteness | | sample | measured value Degree of whiteness | |
|---|---|---|---|---|---|
| | original powder | after standing for 6 months | | original powder | after standing for 6 months |
| example 1-1 | 93.84 | 91.25 | example 1-2 | 91.69 | 90.01 |
| control 1-1 | 93.32 | 89.98 | control 1-2 | 88.13 | 86.22 |
| T 1-1 | 87.63 | 82.07 | T 1-2 | 85.18 | 82.68 |
| H 1-1 | 87.84 | 81.73 | H 1-2 | 83.23 | 80.21 |
| example 2-1 | 87.21 | 82.14 | example 2-2 | 82.70 | 79.15 |
| control 2-1 | 87.49 | 77.40 | control 2-2 | 79.25 | 75.10 |
| T 2-1 | 75.86 | 62.01 | T 2-2 | 71.16 | 64.30 |
| H 2-1 | 74.64 | 60.03 | H 2-2 | 69.45 | 63.21 |
| example 3-1 | 68.65 | 58.81 | example 3-2 | 79.26 | 77.24 |
| control 3-1 | 62.55 | 41.05 | control 3-2 | 73.61 | 70.33 |
| T 3-1 | 54.47 | 30.57 | T 3-2 | 58.71 | 48.49 |
| H 3-1 | 53.25 | 28.91 | H 3-2 | 55.55 | 50.84 |
| example 4-1 | 65.27 | 49.66 | example 4-2 | 72.43 | 69.25 |
| control 4-1 | 61.20 | 33.20 | control 4-2 | 67.11 | 61.87 |
| T 4-1 | 50.64 | 22.73 | T 4-2 | 55.22 | 48.23 |
| H 4-1 | 50.44 | <20 | H 4-2 | 53.22 | 39.55 |
| example 5-1 | 61.82 | 40.31 | example 5-2 | 64.90 | 60.55 |
| control 5-1 | 58.45 | 21.62 | control 5-2 | 62.07 | 55.26 |
| T 5-1 | 47.47 | <20 | T 5-2 | 51.52 | 35.67 |
| H 5-1 | 46.17 | <20 | H 5-2 | 48.01 | 36.86 |

TABLE 2

| metal and amount carried | carrier | Degree of whiteness | | | |
|---|---|---|---|---|---|
| | | not heat fired | | 1200° C. heat fired | |
| | | original powder | after standing for 6 months | original powder | after standing for 6 months |
| silver 2% | calcium secondary phosphate | 57.49 | 25.32 | 58.16 | 45.92 |
| | calcium pyro phosphate | 52.93 | 27.40 | 51.36 | 44.00 |
| silver 2% zinc 2% | calcium secondary phosphate | 64.32 | 37.36 | 76.01 | 67.33 |
| | calcium pyro phosphate | 60.06 | 36.87 | 69.66 | 66.18 |

What is claimed is:

1. An antibacterial composition of calcium tertiary phosphate having adsorbed silver, zinc thereon and/or ions thereof, wherein the amount of silver adsorbed on said calcium tertiary phosphate is from 0.0001 to 10% by weight with respect to said calcium tertiary phosphate and the amount of zinc adsorbed on said calcium tertiary phosphate is more than 5% by weight with respect to the amount of silver adsorbed on said calcium tertiary phosphate to prevent discoloration of said antibacterial composition.

2. The antibacterial composition of claim 1, which is heat-fired at a temperature of not less than 960° C.

3. A method for preventing discoloration of an antibacterial composition of calcium tertiary phosphate having adsorbed thereon siliver and/or ions thereof in an amount from 0.0001 to 10% by weight with respect to said calcium tertiary phosphate said method comprising adding zinc and/or ions thereof to said composition in an amount more than 5% by weight with respect to the amount of silver carried on said calcium tertiary phosphate.

4. The process of claim 3 wherein said composition with said zinc is heat-fired at a temperature of not less than 960° C.

* * * * *